United States Patent
Frijlink

(10) Patent No.: US 6,872,723 B2
(45) Date of Patent: Mar. 29, 2005

(54) STABILIZED DIFLOXACIN INJECTABLE SOLUTION

(75) Inventor: Henderik W. Frijlink, 9761 KM Eelde (NL)

(73) Assignee: Wyeth, Madison, NJ (US)

(*) Notice: Subject to any disclaimer, the term of this patent is extended or adjusted under 35 U.S.C. 154(b) by 0 days.

(21) Appl. No.: 10/346,597

(22) Filed: Jan. 17, 2003

(65) Prior Publication Data

US 2003/0153581 A1 Aug. 14, 2003

Related U.S. Application Data

(60) Provisional application No. 60/352,764, filed on Jan. 28, 2002.

(51) Int. Cl.$^7$ .............................................. A61K 31/497
(52) U.S. Cl. ........................... 514/253.08; 514/253.07; 514/253.06
(58) Field of Search ....................... 514/253.08, 253.07, 514/253.06

(56) References Cited

U.S. PATENT DOCUMENTS

| 4,772,605 A | | 9/1988 | Naik et al. | |
|---|---|---|---|---|
| 5,756,506 A | * | 5/1998 | Copeland et al. | 514/254.11 |

FOREIGN PATENT DOCUMENTS

JP          1995-82141          3/1995

* cited by examiner

Primary Examiner—Kevin E. Weddington
(74) Attorney, Agent, or Firm—Barbara L. Renda; Anne M. Rosenblum

(57) ABSTRACT

An antibacterial formulation suitable for injection into animals containing approximately 2–10% w/v difloxacin HCl, L-arginine base, propylene glycol, ethanol and/or benzyl alcohol, and water. The formulation is a solution having a pH of form 9 to 10. The formulation produces little or no tissue damage or irritation at the injection site.

10 Claims, No Drawings

STABILIZED DIFLOXACIN INJECTABLE SOLUTION

FIELD OF THE INVENTION

This application claims priority from copending provisional application Ser. No. 60/352,764, filed on Jan. 28, 2002, the entire disclosure of which is hereby incorporated by reference. This invention relates to the field of formulations for the antibiotic compound difloxacin, especially formulations suitable to be injected into animals.

BACKGROUND OF THE INVENTION

Difloxacin, also known as 6-fluoro-1-(4-fluorophenyl)-1,4-dihydro-7-(4-methyl-1-piperadinyl) 4-oxo-3-quinolinecarboxylic acid, is an antibiotic compound useful against a wide range of bacteria in animals. However, it is not highly soluble in water, which makes difloxacin difficult to formulate for administration by injection. Difloxacin is soluble in some high pH formulations, but high pH formulations tend to damage or irritate the tissue at the injection site.

U.S. Pat. No. 4,772,605 teaches alkaline aqueous formulations for quinolinecarboxylic acids which contain arginine and a base, and may contain an alcohol and/or other ingredients. Formulations containing difloxacin are not disclosed in this patent.

U.S. Pat. No. 5,756,506 teaches the administration of a single high dose of a fluoroquinolone composition, especially an enrofloxacin composition, for treating bacterial infections in animals.

Japanese patent application no. 232024 (1993), published as no. JP 07082141, discloses an injectable aqueous formulation containing difloxacin, a base, and propylene glycol, and optionally benzyl alcohol. This formulation allegedly reduces tissue damage at the injection site.

SUMMARY OF THE INVENTION

The present invention is a formulation suitable for injection into animals comprising approximately 2–10% w/v difloxacin HCl, L-arginine base, propylene glycol, ethanol and/or benzyl alcohol, and water. The present invention also comprises a method for making such a formulation.

It is an object of the present invention to provide a difloxacin formulation which is suitable for injection into animals and which will not significantly damage the tissue at the injection site.

Other objects and advantages of the present invention will be apparent to those skilled in the art from the disclosure below and the appended claims.

DETAILED DESCRIPTION OF THE PREFERRED EMBODIMENTS

A preferred embodiment of the present invention is a formulation comprising approximately: 4–6% difloxacin HCl; 20–40% propylene glycol; 5–15% L-arginine base; 5–15% ethanol; 0–10% benzyl alcohol; and water. These percentages are on a weight/volume (w/v) basis, i.e., g/ml. The measured pH is preferably in the approximate range of 9–10, and more preferably in the approximate range of 9.1–9.6.

A highly preferred embodiment of the present invention comprises approximately: 5% (w/v) difloxacin HCl; 30% (w/v) propylene glycol; 10% (w/v) L-arginine base; 10% (w/v) ethanol; 5% (w/v) benzyl alcohol; and water.

The pH of the formulation may be adjusted to achieve the desired level of alkalinity by addition of an acid or base. Any suitable acid or base may be used. Bases such as potassium hydroxide, and acids such as HCl, have been found to be highly suitable for this purpose. Those skilled in the art will have no difficulty identifying suitable bases or acids.

The desired pH level may be achieved not only with L-arginine base, but alternatively with either glycine in combination with KOH, or with diethanolamine. The use of L-arginine is preferred I the practice of this invention.

Although propylene glycol is most preferred, it may be partly or wholly replaced by similar compounds, such as glycerol and soluble polyethylene glycols, e.g., polyethylene glycol 400, and the like.

Benzyl alcohol may act as both a co-solvent and an antimicrobial preservative in the formulation of this invention. The benzyl alcohol may be partly or wholly replaced by one or more other preservatives known in the art, such as chlorocresol and phenol. However, benzyl alcohol is preferred.

Preferably, the formulation of this invention is made by adding the difloxacin HCl and arginine to water at room temperature, mixing until a uniform suspension is achieved, and then mixing in the ethanol, benzyl alcohol and propylene glycol until the solids dissolve. The exact temperature is not critical, as long as it is not too cold to hinder dissolution of the solids or hot enough to adversely affect the components of the formulation or cause significant evaporation of the ethanol. A temperature of approximately 10–30° C. is suitable for formulating the composition of this invention; a temperature of about 15–25° C. is preferred, and 18–25° C. is more preferred. The pH may be adjusted, if necessary, for example with HCl or KOH, to achieve the desired level of alkalinity.

The arginine acts as a buffer and helps to achieve a suitable pH at which the difloxacin will fully dissolve. In a preferred embodiment of the invention, approximately 5–20% w/v L-arginine is used; 5–15% is more preferred, and 10% is most preferred. The glycol and alcohols are used to facilitate the solubility of the difloxacin so that a higher pH is not needed. The more moderate pH may prevent or reduce tissue damage and discomfort at the injection site.

Formulations having a difloxacin concentration significantly higher than about 5–6% may provide decreased bioavailability of difloxacin after administration by injection. Formulations containing greater than about 10% difloxacin may be made, but such formulations may require a disadvantageously high pH level and may have less desirable pharmacokinetics than formulations of this invention.

Although the use of difloxacin HCl is described herein, other forms of difloxacin may be used. If, for example, the base difloxacin is used instead of difloxacin HCl, less argenine and/or other base is needed to achieve the desired pH. Those skilled in the art will easily be able to determine how much base is needed to achieve a pH within the range set forth herein for this invention, regardless of the form of the difloxacin. Those skilled in the art will also recognize that other salts of difloxacin are pharmaceutically suitable substitutes for the hydrochloride salt, and will be able to identify and use such salts in this invention without undue experimentation. The desired pH range can be achieved, regardless of the form of difloxacin used, by using the requisite amount of HCl or KOH to adjust pH.

The formulation of the present invention has the advantage that it may be formulated without the need for heating to dissolve the solid ingredients. In fact, heating may be detrimental to dissolution of the difloxacin, since it may cause evaporation of a significant amount of the ethanol.

The formulation of this invention is stable when stored under normal conditions used in the art. The storage temperature may be lower than 10° C., e.g., 5° C. or less, as long as a precipitate does not form. Those skilled in the art will have no difficulty determining suitable storage temperatures.

The present invention provides a formulation in which the difloxacin is completely dissolved, which minimizes tissue damage at the injection site, and which has the advantage of rapid and essentially complete bioavailability of the active ingredient. The production of the formulation of this invention is quite robust, especially when ethanol is used as the solvent; it has been found that if the pH rises temporarily above 11.0 during production, ethanol prevents insoluble precipitates from forming.

The pH of the solution of this invention is believed to be very important in providing a formulation that: (a) minimizes damage or irritation to the tissue at the injection site; (b) dissolves the difloxacin; and, (c) produces a relatively high blood plasma level of difloxacin in the first two hours after administration by injection.

The various advantages of this invention are achieved using a combination of ingredients which facilitate dissolution of the difloxacin at a relatively moderate level of alkalinity, and which cause minimal irritation at the injection site. Surprisingly, although the formulation of this invention contains high levels of several ingredients that are known to be irritating to tissue, the combination of ingredients in the present invention result in an unexpectedly low level of irritation.

The following examples are presented to illustrate certain embodiments of the present invention, but should not be construed as limiting the scope of this invention.

EXAMPLE 1

The following ingredients are used to create a difloxacin solution for injection:

|  | % (m/v) |
| --- | --- |
| difloxacin HCl | 5.46 (=5.0% free base) |
| propylene glycol | 30.0 |
| benzyl alcohol | 5.0 |
| ethanol | 10.0 |
| L-arginine base | 10.0 |
| water q.s. | to 100%. |

About 80% of the water for injection is charged to a vessel and maintained at 18–25° C. The arginine and difloxacin HCl are added with mixing to form a uniform suspension, and the vessel is purged with nitrogen gas. The ethanol, propylene glycol and benzyl alcohol are added and the composition is mixed until the solids dissolve. The rest of the water for injection is added with mixing to reach the full volume. The solution is sterilized using saturated steam at 121° C. for 30 minutes. The pH of the solution is 9.3. The solution is clear and no precipitate is observed. The osmolarity (mOsmol/Kg, after a 10-fold dilution with water for injection) is 723.

EXAMPLE 2

Compositions having 2.5% and 6% difloxacin (w/v) are prepared according to the procedure of Example 1, and the pH is adjusted with either KOH or HCl, if necessary, to reach a pH of 9.9. In these solutions, the percentage of the ingredients other than difloxacin and water are the same as in Example 1.

EXAMPLE 3

The three difloxacin compositions prepared according to Examples 1 and 2 are used in an experiment to study the pharmacokinetics of these formulations when injected into sheep. Twelve male lambs about 10 months old are divided into three groups of four; a different formulation of Examples 1 and 2 is administered to each group. The lambs are each injected with one of the formulations at a dose of 2.5 mg/kg body weight, and blood samples are taken at 1, 2, 4, 6, 10 and 24 hours after injection. Mean plasma levels ($\mu$g/ml) for these samples are provided in the table below:

|  | Hours after injection: | | | | | |
| --- | --- | --- | --- | --- | --- | --- |
|  | 1 | 2 | 4 | 6 | 10 | 24 |
| 2.5% difloxacin formulation | 877 | 860 | 648 | 500 | 339 | 131 |
| 5% difloxacin formulation | 1097 | 1108 | 812 | 578 | 371 | 98 |
| 6% difloxacin formulation | 617 | 705 | 658 | 547 | 381 | 142 |

These formulations do not produce significant tissue damage or swelling at the injection site. The 5% difloxacin formulation having a measured pH=9.3 produces a significantly higher level of difloxacin in the blood in the first 1–4 hours after injection than either the 2.5% or 6% formulations having a measured pH of 9.9.

EXAMPLE 4

A formulation is prepared according to Example 1, except that the difloxacin content is doubled to form a 10% w/v solution, and the final pH is 9.9.

EXAMPLES 5 & 6

Two 5% w/v difloxacin formulations are prepared according to Example 1, except that the final pH is 9.1 and 9.6, respectively. The pH is adjusted using KOH or HCl to obtain the desired pH value.

Comparative Examples

A 5% difloxacin formulation is made according to the procedure in Example 1, with the exception that the ethanol is omitted and the final pH is 9.9. This formulation is administered to three male lambs in accordance with the procedure of Example 3, with the following results:

|  | Hours after injection: | | | | | |
| --- | --- | --- | --- | --- | --- | --- |
|  | 1 | 2 | 4 | 6 | 10 | 24 |
| Mean blood plasma level ($\mu$g/ml). | 783 | 955 | 824 | 650 | 438 | 117 |

The blood plasma level in the first two hours is less than that produced by administering the formulation of Example 1. These results indicate that the use of ethanol and a lower pH according to the present invention provides a superior formulation compared to the formulation of this Comparative Example having the same difloxacin content.

Many variations of the present invention not illustrated herein will occur to those skilled in the art. The present invention is not limited to the embodiments illustrate and described herein, but encompasses all the subject matter within the scope of the appended claims and equivalents thereof.

What is claimed is:

1. A pharmaceutical composition suitable for injection into an animal, said composition comprising: about 2–10% w/v difloxacin HCl; 5–20% w/v L-arginine base; about 5–15% w/v ethanol; up to about 10% w/v of an anti-microbial preservative; propylene glycol, glycerol, a soluble polyethylene glycol, or a combination thereof; and water, wherein said composition has a pH in the approximate range of 9–10.

2. A composition according to claim 1, wherein said difloxacin HCl concentration is about 4–6% difloxacin HCl.

3. A composition according to claim 2, comprising approximately 20–40% propylene glycol and 5–15% L-arginine base, wherein said anti-microbial preservative is selected from the group consisting of benzyl alcohol, phenol, chlorocresol, and mixtures thereof.

4. A composition according to claim 3 wherein the pH is in the approximate range of 9.1–9.6.

5. A composition according to claim 3 wherein said preservative is benzyl alcohol.

6. A composition according to claim 2 wherein the pH is in the approximate range of 9.1–9.6.

7. A composition according to claim 1 wherein the pH is in the approximate range of 9.1–9.6.

8. A composition according to claim 1 further comprising potassium hydroxide.

9. A composition according to claim 8 wherein said preservative is benzyl alcohol, and the pH is in the approximate range of 9.1–9.6.

10. A pharmaceutical composition suitable for injection into an animal, said composition comprising: about 5% w/v difloxacin HCl; 10% w/v L-arginine base; about 10% w/v ethanol; about 5% w/v benzyl alcohol; about 30% w/v propylene glycol; and water, wherein said composition has a pH in the approximate range of 9.1–9.6.

* * * * *